(12) United States Patent
Norton et al.

(10) Patent No.: US 8,030,632 B2
(45) Date of Patent: Oct. 4, 2011

(54) CONTROLLING ANGLE OF INCIDENCE OF MULTIPLE-BEAM OPTICAL METROLOGY TOOLS

(75) Inventors: Adam Norton, Palo Alto, CA (US); Xinkang Tian, San Jose, CA (US)

(73) Assignee: Tokyo Electron Limted, Tokyo (JP)

( * ) Notice: Subject to any disclaimer, the term of this patent is extended or adjusted under 35 U.S.C. 154(b) by 393 days.

(21) Appl. No.: 12/414,637

(22) Filed: Mar. 30, 2009

(65) Prior Publication Data

US 2010/0243860 A1 Sep. 30, 2010

(51) Int. Cl.
*G01J 4/00* (2006.01)
(52) U.S. Cl. ............... 250/559.08; 356/364; 356/445
(58) Field of Classification Search .... 250/201.1–201.9, 250/559.01–559.08; 356/364, 369, 237.1, 356/237.2–237.5, 448
See application file for complete search history.

(56) References Cited

U.S. PATENT DOCUMENTS

| | | | |
|---|---|---|---|
| 4,705,940 A * | 11/1987 | Kohno | 355/55 |
| 5,166,752 A | 11/1992 | Spanier et al. | |
| 5,412,473 A | 5/1995 | Rosencwaig et al. | |
| 5,486,701 A * | 1/1996 | Norton et al. | 250/372 |
| 5,596,406 A | 1/1997 | Rosencwaig et al. | |
| 5,747,813 A * | 5/1998 | Norton et al. | 250/372 |
| 5,798,837 A | 8/1998 | Aspnes et al. | |
| 6,184,984 B1 * | 2/2001 | Lee et al. | 356/369 |
| 6,256,097 B1 | 7/2001 | Wagner | |
| 6,297,880 B1 * | 10/2001 | Rosencwaig et al. | 356/369 |
| 6,429,943 B1 | 8/2002 | Opsal et al. | |
| 6,778,273 B2 * | 8/2004 | Norton et al. | 356/364 |
| 6,785,638 B2 | 8/2004 | Niu et al. | |
| 6,798,512 B2 | 9/2004 | Ebert et al. | |
| 6,891,626 B2 | 5/2005 | Niu et al. | |
| 6,943,900 B2 | 9/2005 | Niu et al. | |
| 6,972,419 B2 * | 12/2005 | Tejnil | 250/492.2 |
| 7,006,221 B2 | 2/2006 | Wolf et al. | |
| 7,081,957 B2 | 7/2006 | Norton | |
| 7,280,229 B2 | 10/2007 | Li et al. | |
| 7,331,676 B2 * | 2/2008 | Ferber et al. | 353/20 |
| 7,502,101 B2 | 3/2009 | Raymond et al. | |

OTHER PUBLICATIONS

U.S. Appl. No. 12/050,053, filed Mar. 17, 2008 for Tian et al.
U.S. Appl. No. 12/050,919, filed Mar. 18, 2008 for Tian et al.
U.S. Appl. No. 12/057,316, filed Mar. 27, 2008 for Tian et al.
U.S. Appl. No. 12/057,332, filed Mar. 27, 2008 for Tian et al.

(Continued)

*Primary Examiner* — Tony Ko
(74) *Attorney, Agent, or Firm* — Manuel Madriaga

(57) ABSTRACT

Provided is a method of controlling multiple beams directed to a structure in a workpiece, the method comprising generating a first illumination beam with a first light source and a second illumination beam with a second light source, projecting the first and second illumination beams onto a separate illumination secondary mirror, reflecting the first and second illumination beams onto an illumination primary mirror, the reflected first and second illumination beams projected onto the structure at a first and second angle of incidence respectively, the reflected first and second illumination beams generating a first and second detection beams respectively. The separate illumination secondary mirror is positioned relative to the illumination primary mirror so as make the first angle of incidence substantially the same or close to a calculated optimum first angle of incidence and make the second angle of incidence substantially the same or close to a calculated optimum second angle of incidence. The first and second detection beams are diffracted off the structure at the corresponding angle of incidence to a detection primary mirror, reflected onto a separate secondary detection mirror and other optical components on the detection path, and onto spectroscopic detectors.

20 Claims, 12 Drawing Sheets

OTHER PUBLICATIONS

U.S. Appl. No. 12/057,346, filed Mar. 27, 2008 for Tian et al.
U.S. Appl. No. 12/059,610, filed Mar. 31, 2008 for Meng et al.
U.S. Appl. No. 12/141,754, filed Jun. 18, 2008 for Tian et al.
U.S. Appl. No. 12/141,867, filed Jun. 18, 2008 for Tian et al.
U.S. Appl. No. 12/141,892, filed Jun. 18, 2008 for Tian et al.
U.S. Appl. No. 12/413,945, filed Mar. 30, 2009 for Norton et al.
U.S. Appl. No. 12/414,462, filed Mar. 30, 2009 for Li et al.

* cited by examiner

CONTROLLING ANGLE OF INCIDENCE OF MULTIPLE-BEAM OPTICAL METROLOGY TOOLS

BACKGROUND

1. Field of Invention

The present application generally relates to the design of an optical metrology tool to measure a structure formed on a workpiece, and, more particularly, to a method and an apparatus for controlling angles of incidence (AOI) of multiple illumination beams in an objective lens assembly and a method of optimizing optical metrology measurement sensitivity.

2. Related Art

Optical metrology involves directing an incident beam at a structure on a workpiece, measuring the resulting diffraction signal, and analyzing the measured diffraction signal to determine various characteristics of the structure. The workpiece can be a wafer, a substrate, photomask or a magnetic medium. In manufacturing of the workpieces, periodic gratings are typically used for quality assurance. For example, one typical use of periodic gratings includes fabricating a periodic grating in proximity to the operating structure of a semiconductor chip. The periodic grating is then illuminated with an electromagnetic radiation. The electromagnetic radiation that deflects off of the periodic grating are collected as a diffraction signal. The diffraction signal is then analyzed to determine whether the periodic grating, and by extension whether the operating structure of the semiconductor chip, has been fabricated according to specifications.

In one conventional system, the diffraction signal collected from illuminating the periodic grating (the measured diffraction signal) is compared to a library of simulated diffraction signals. Each simulated diffraction signal in the library is associated with a hypothetical profile. When a best match is made between the measured diffraction signal and one of the simulated diffraction signals in the library, the hypothetical profile associated with the simulated diffraction signal is presumed to represent the actual profile of the periodic grating. The hypothetical profiles, which are used to generate the simulated diffraction signals, are generated based on a profile model that characterizes the structure to be examined. Thus, in order to accurately determine the profile of the structure using optical metrology a profile model that accurately characterizes the structure should be used.

With increased requirement for increasing the measurement accuracy and sensitivity, throughput, decreasing size of the test structures, smaller spot sizes, and lower cost of ownership, there is greater need to optimize design of optical metrology systems to meet several design goals. Characteristics of the optical metrology system including throughput, range of measurement capabilities, accuracy and repeatability of diffraction signal measurements are essential to meeting the increased requirement for measurement sensitivity, smaller spot size and lower cost of ownership of the optical metrology system. Selection of number of illumination beams, light sources, angle of incidence, and optimization of other optical design parameters, such as wavelength range contribute to the above objectives.

SUMMARY

Provided is a method of controlling multiple beams directed to a structure in a workpiece, the method comprising generating a first illumination beam with a first light source and a second illumination beam with a second light source, projecting the first and second illumination beams onto a separate illumination secondary mirror, reflecting the first and second illumination beams onto an illumination primary mirror, the reflected first and second illumination beams projected onto the structure at a first and second angle of incidence respectively, the reflected first and second illumination beams generating a first and second detection beams respectively. The separate illumination secondary mirror is positioned relative to the illumination primary mirror so as make the first angle of incidence substantially the same or close to a calculated optimum first angle of incidence and make the second angle of incidence substantially the same or close to a calculated optimum second angle of incidence. The first and second detection beams are diffracted off the structure at the corresponding angle of incidence to a detection primary mirror, reflected onto a separate secondary detection mirror and other optical components on the detection path, and onto spectroscopic detectors.

BRIEF DESCRIPTION OF DRAWINGS

FIG. 5A depicts an exemplary top-view of an architectural diagram of an objective lens assembly using separate illumination and detection convex secondary mirrors for two illumination beams whereas

FIG. 6A depicts an exemplary flowchart of a method of determining profile parameters of a structure with an objective lens assembly using separate illumination and detection convex secondary mirrors for two illumination beams whereas

DETAILED DESCRIPTION

Figure 1:
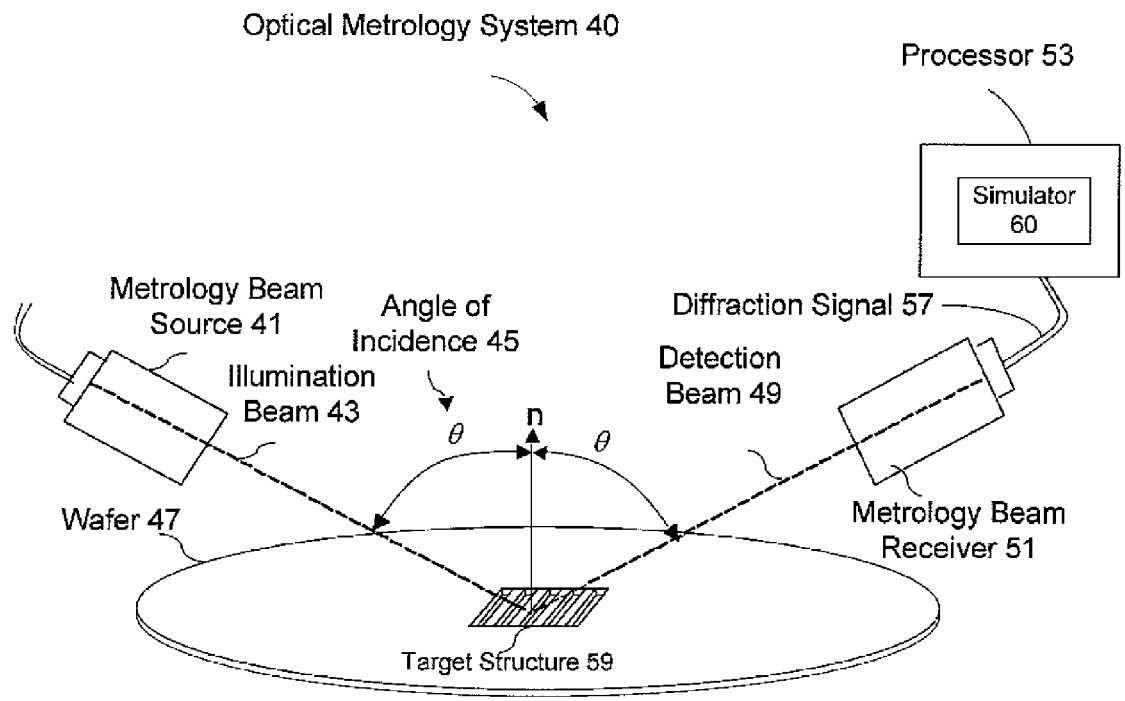
FIG. 1 is an architectural diagram illustrating an exemplary embodiment where an optical metrology system can be utilized to determine the profiles of structures formed on a semiconductor wafer.

In order to facilitate the description of the present invention, a semiconductor wafer may be utilized to illustrate an application of the concept. The systems and processes equally apply to other workpieces that have reflective surfaces. The workpiece may be a wafer, a substrate, photomask, magnetic medium or the like. Furthermore, in this application, the term structure when it is not qualified refers to a patterned structure. In the following description, for purposes of explanation and not limitation, specific details are set forth, such as a particular geometry or layout of an optical metrology system, descriptions of various components and methods used therein. Reference throughout this specification to "one embodiment" or "an embodiment" means that a particular feature, structure, material, or characteristic described in connection with the embodiment is included in at least one embodiment of the invention, but do not denote that they are present in every embodiment. Thus, the appearances of the phrases "in one embodiment" or "in an embodiment" in various places throughout this specification are not necessarily referring to the same embodiment of the invention. Furthermore, the particular features, structures, materials, or characteristics may be combined in any suitable manner in one or more embodiments. It should be understood that the invention may be practiced in other embodiments that depart from these specific details. Referring now to the drawings, like reference numerals designate identical or corresponding parts throughout the several views.

FIG. 1 is an architectural diagram illustrating an exemplary embodiment where optical metrology can be utilized to determine the profiles or shapes of structures fabricated on a semiconductor wafer. The optical metrology system 40 includes a metrology beam source 41 projecting a metrology illumination beam 43 at the target structure 59 of a wafer 47. The metrology beam 43 is projected at an incidence angle θ towards the target structure 59. The diffracted detection beam 49 is measured by a metrology beam receiver 51. A measured diffraction signal 57 is transmitted to a processor 53. The processor 53 compares the measured diffraction signal 57 against a simulator 60 of simulated diffraction signals and associated hypothetical profiles representing varying combinations of critical dimensions of the target structure and resolution. The simulator can be either a library that consists of a machine learning system, pre-generated data base and the like (this is library system), or on demand diffraction signal generator that solves the Maxwell equation for a giving profile (this is regression system). In one exemplary embodiment, the diffraction signal generated by the simulator 60 instance best matching the measured diffraction signal 57 is selected. The selected hypothetical profile and associated critical dimensions of the selected simulator 60 instance are assumed to correspond to the actual cross-sectional shape and critical dimensions of the features of the target structure 59. The optical metrology system 40 may utilize a reflectometer, an ellipsometer, or other optical metrology device to measure the diffraction beam or signal. An optical metrology system is described in U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety.

Simulated diffraction signals can be generated by applying Maxwell's equations and using a numerical analysis technique to solve Maxwell's equations. It should be noted that various numerical analysis techniques, including variations of RCWA, can be used. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

Simulated diffraction signals can also be generated using a machine learning system (MLS). Prior to generating the simulated diffraction signals, the MLS is trained using known input and output data. In one exemplary embodiment, simulated diffraction signals can be generated using an MLS employing a machine learning algorithm, such as back-propagation, radial basis function, support vector, kernel regression, and the like. For a more detailed description of machine learning systems and algorithms, see U.S. patent application Ser. No. 10/608,300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

Figure 2:
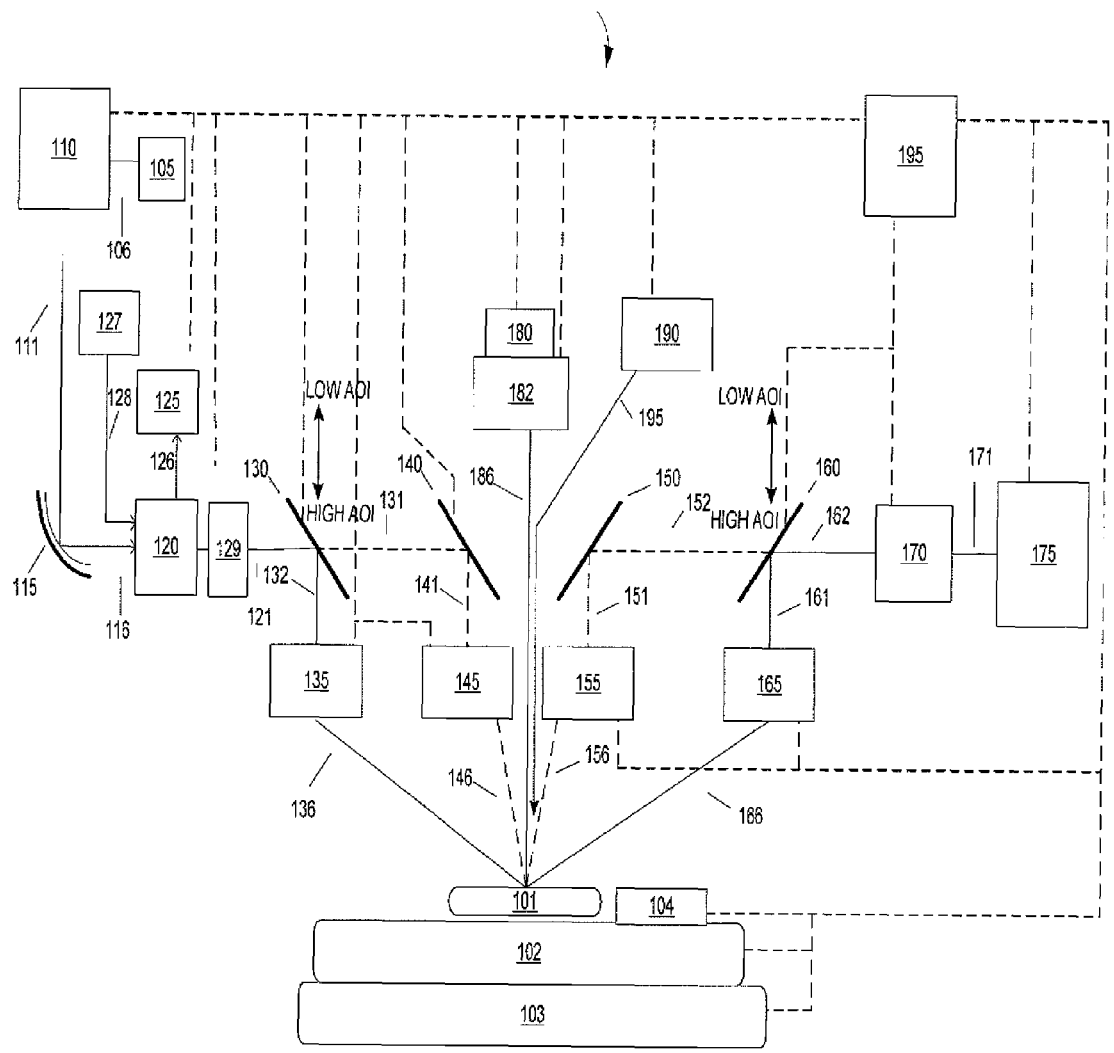
FIG. 2 depicts an exemplary optical metrology system in accordance with embodiments of the invention.

FIG. 2 shows an exemplary block diagram of an optical metrology system in accordance with embodiments of the invention. In the illustrated embodiment, an optical metrology system 100 can comprise a lamp subsystem 105, and at least two optical outputs 106 from the lamp subsystem 105 can be transmitted to an illuminator subsystem 110. The lamp subsystem 105 may include a first lamp, for example, a deuterium lamp generating an illumination beam with a plurality of wavelengths. The wavelength range may be 180 to 400 nm or 180 to 350 nm. Other wavelength ranges can be used. The lamp subsystem 105 may also include a second lamp, for example, a xenon lamp generating an illumination beam with a plurality of wavelengths. The wavelength range may be 200 to 900 nm or 250 to 900 nm. Other wavelength ranges can be used. Alternatively, lamp subsystem 105 may include other light sources or combinations of light sources and other combinations of wavelength ranges.

At least two optical outputs 111 from the illuminator subsystem 110 can be transmitted to a selector subsystem 115. The selector subsystem 115 can send at least two signals 116 to a beam generator subsystem 120. In addition, a reference beam 126 is split from the main beam 116 and directed to subsystem 125 that can be used to provide reference outputs. A second calibration subsystem 127 provides a wavelength calibration lamp that can be used as a source to generate calibration beam 128, the source selected between the illuminator subsystem 110 and calibration subsystem 127, for example, with a flip-in mirror (not shown). The wafer 101 is positioned using an X-Y-Z-theta stage 102 where the wafer 101 is adjacent to a wafer alignment sensor 104, supported by a platform base 103.

The optical metrology system 100 can comprise a polarizer subsystem 129 and a first selectable reflection subsystem 130 that can be used to direct at least two outputs 121 from the polarizer subsystem 129 on a first path 131 when operating in a first mode "LOW AOI" or on a second path 132 when operating in a second mode "HIGH AOI". When the first selectable reflection subsystem 130 is operating in the first mode "LOW AOI", at least two of the outputs 121 from the polarizer subsystem 129 can be directed to a first reflection subsystem 140 as outputs 131, and at least two outputs 141 from the first reflection subsystem can be directed to a low angle-focusing subsystem 145, When the first selectable reflection subsystem 130 is operating in the second mode "HIGH AOI", at least two of the outputs 121 from the polarizer subsystem 129 can be directed to a high angle focusing subsystem 135 as outputs 132. Alternatively, other modes in addition to "LOW AOI" and "HIGH AOI" may be used and other configurations may be used.

When the metrology system 100 is operating in the first mode "LOW AOI", at least two of the outputs 146 from the low angle focusing subsystem 145 can be directed to the wafer 101. For example, a low angle of incidence can be used.

When the metrology system 100 is operating in the second mode "HIGH AOI", at least two of the outputs 136 from the high angle focusing subsystem 135 can be directed to the wafer 101. For example, a high angle of incidence can be used. Alternatively, other modes may be used and other configurations may be used.

The optical metrology system 100 can comprise a low angle collection subsystem 155, a high angle collection subsystem 165, a second reflection subsystem 150, and a second selectable reflection subsystem 160.

When the metrology system 100 is operating in the first mode "LOW AOI", at least two of the outputs 156 from the wafer 101 can be directed to the low angle collection subsystem 155. For example, a low angle of incidence can be used. In addition, the low angle collection subsystem 155 can process the outputs 156 obtained from the wafer 101 and low angle collection subsystem 155 can provide outputs 151 to the second reflection subsystem 150, and the second reflection subsystem 150 can provide outputs 152 to the second selectable reflection subsystem 160. When the second selectable reflection subsystem 160 is operating in the first mode "LOW AOI" the outputs 152 from the second reflection subsystem 150 can be directed to the analyzer subsystem 170. For example, at blocking elements can be moved allowing the outputs 152 from the second reflection subsystem 150 to pass through the second selectable reflection subsystem 160 with a minimum amount of loss.

When the metrology system 100 is operating in the second mode "HIGH AOI", at least two of the outputs 166 from the wafer 101 can be directed to the high angle collection subsystem 165. For example, a high angle of incidence can be used. In addition, the high angle collection subsystem 165 can process the outputs 166 obtained from the wafer 101 and high angle collection subsystem 165 can provide outputs 161 to the second selectable reflection subsystem 160. When the second selectable reflection subsystem 160 is operating in the second mode "HIGH AOI" the outputs 162 from the second selectable reflection subsystem 160 can be directed to the analyzer subsystem 170.

When the metrology system 100 is operating in the first mode "LOW AOI", low incident angle, the output beam 162 is directed to the analyzer subsystem 170, and when the metrology system 100 is operating in the second mode "HIGH AOI", high incident angle data from the wafer 101, output beam 162, generated from output beam 161, is directed to the analyzer subsystem 170.

Metrology system 100 can include at least two measurement subsystems 175. At least two of the measurement subsystems 175 can include at least two detectors such as spectrometers. For example, the spectrometers can operate from the Deep-Ultra-Violet to the visible regions of the spectrum.

The metrology system 100 can include a camera subsystems 180, illumination and imaging subsystems 182 coupled to the camera subsystems 180. In some embodiments, the metrology system 100 can include auto-focusing subsystems 190. Alternatively, other focusing techniques may be used.

One or more of the controllers (not shown) in at least one of the subsystems (105, 110, 115, 120, 125, 130, 135, 140, 145, 150, 155, 160, 165, 170, 175, 180, 182, 190, and 195) can be used when performing measurements of the structures. A controller can receive real-signal data to update subsystem, processing element, process, recipe, profile, image, pattern, and/or model data. One or more of the subsystems (105, 110, 115, 120, 125, 130, 135, 140, 145, 150, 155, 160, 165, 170, 175, 180, 182, and 190) can exchange data using at least two Semiconductor Equipment Communications Standard (SECS) messages, can read and/or remove information, can feed forward, and/or can feedback the information, and/or can send information as a SECS message.

Those skilled in the art will recognize that one or more of the subsystems (105, 110, 115, 120, 125, 130, 135, 140, 145, 150, 155, 160, 165, 170, 175, 180, 182, 190, and 195) can include computers and memory components (not shown) as required. For example, the memory components (not shown) can be used for storing information and instructions to be executed by computers (not shown) and may be used for storing temporary variables or other intermediate information during the execution of instructions by the various computers/processors in the metrology system 100. One or more of the subsystems (105, 110, 115, 120, 125, 130, 135, 140, 145, 150, 155, 160, 165, 170, 175, 180, 185, and 190) can include the means for reading data and/or instructions from a computer readable medium and can comprise the means for writing data and/or instructions to a computer readable medium. The metrology system 110 can perform a portion of or all of the processing steps of the invention in response to the computers/processors in the processing system executing at least two sequences of at least two instructions contained in a memory and/or received in a message. Such instructions may be received from another computer, a computer readable medium, or a network connection. In addition, one or more of the subsystems (105, 110, 115, 120, 125, 130, 135, 140, 145, 150, 155, 160, 165, 170, 175, 180, 182, and 190) can comprise control applications, Graphical User Interface (GUI) components, and/or database components.

It should be noted that the beam when the metrology system 100 is operating in the first mode "LOW AOI" with a low incident angle data from the wafer 101 all the way to the measurement subsystems 175, (output 156, 151, 152, 162, and 171) and when the metrology system 100 is operating in the second mode "HIGH AOI" with a high incident angle data from the wafer 101 all the way to the measurement subsystems 175, (output 166, 161, 162, and 171) is referred to as diffraction signal(s).

Figure 3:
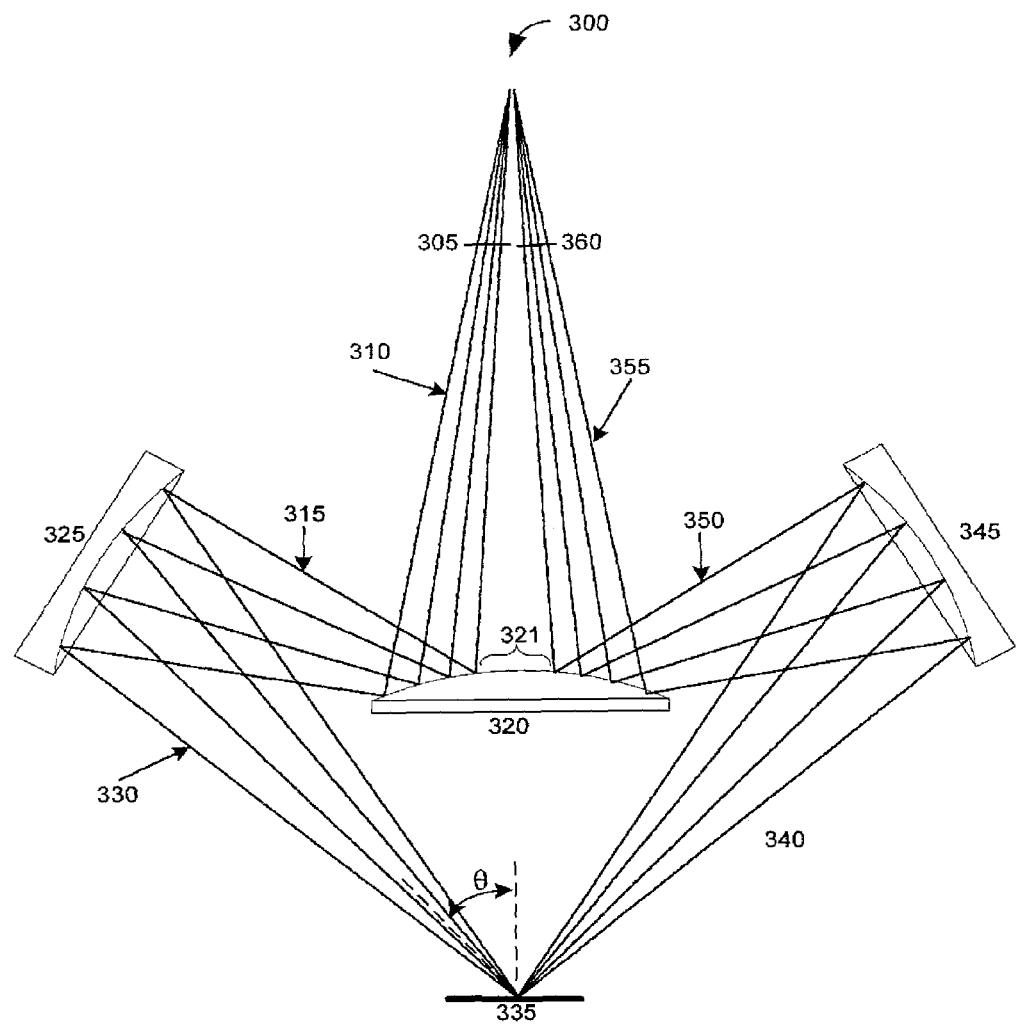
FIG. 3 depicts an exemplary architectural diagram depicting prior art objective lens assembly using a single convex secondary mirror.

FIG. 3 is an architectural diagram depicting prior art objective lens assembly using a single convex secondary mirror for the illumination and detection. The prior art objective lens assembly 300 comprise an illumination source (not shown) that generates a broadband illumination beam 310, the illumination beam 310 passing through an illumination aperture 305 and projected to the secondary convex mirror 320. The illumination beam 310 is reflected by the secondary convex mirror 320 as beam 315 onto a primary illumination mirror 325 and is reflected as illumination beam 330 onto a structure (not shown) on the workpiece 335. The illumination beam 330 is diffracted by the structure on the workpiece 335 as detection beam 340 onto the detection primary mirror 345, reflected as detection beam 350 onto the secondary convex mirror 320 and reflected as detection beam 355, passing through a detection aperture 360 and onto a detector (not shown). Mirrors 325 and 345 are usually combined into one larger spherical mirror. Objective lens assemblies in prior art may include a second illumination beam directed through similar optical components as shown in FIG. 3. A workpiece may include a wafer, substrate, or photomask. The use of a single convex secondary mirror used for illumination and detection does not provide the flexibility of achieving or getting close to an optimum angle of incidence when the numerical aperture of the beam 330 is fixed.

In addition to having an optimum illumination angle of incidence, optical metrology systems will also have an optimum illumination numerical aperture (NA). A larger NA will have the desirable effects of increasing signal strength and decreasing the diffraction-limited spot size on the workpiece, but it will also have the undesired effect of distorting the spectral signal. The NA is thus chosen to be sufficient to produce the required spot size and signal strength, but not too large that it produces a spectral distortion that can not be modeled accurately with reasonable computation effort. Given a particular required NA of beam 330 and other objective design constraints such as the focal length, magnification, working distance, and sensitivity to tolerances, there is a minimum practical value for θ. When the primary and secondary are positioned relative to each other to achieve all other constraints, the edge of the secondary mirror limits the minimum angle θ. This limit can often prevent use of the optimum value for θ.

Figure 4:
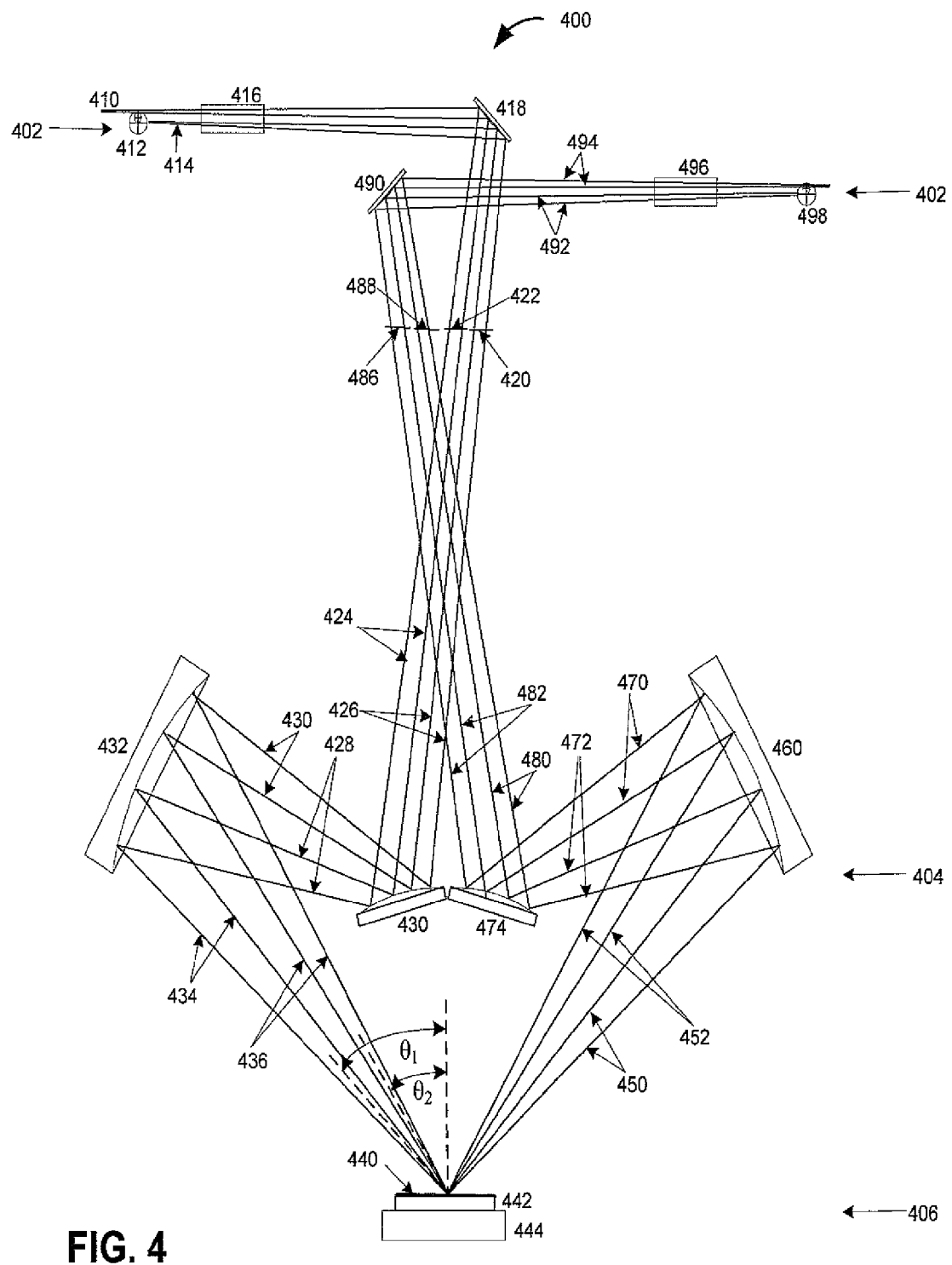
FIG. 4 depicts an architectural diagram depicting an objective lens assembly using separate illumination and detection convex secondary mirrors for two illumination beams.

FIG. 4 is an architectural diagram 400 depicting an optical metrology tool including an objective lens assembly using a separate convex secondary mirror 430 for the illumination beams and another separate convex secondary mirror 474 for the detection beams, in an exemplary embodiment using two illumination beams. The optical metrology tool 400 comprises light sources (not shown), a set of beam separation optics 402 for spatially separating the illumination and detection beams, an illumination polarizer 416, a detection polarizer 496, an objective lens assembly 404 and a motion control system 406 comprising a tilting device 442 and a stage 444. The set of beam separation optics 402 comprises a knife-edge mirror 412, an illumination faceted mirror 418, a detection faceted mirror 490, and a detection knife-edged mirror 498. The first illumination source (not shown) generates a first illumination beam 410 directed to the illumination polarizer 416 and onto illumination faceted mirror 418. The second illumination source (not shown) generates a second illumination beam 414, reflected by knife-edge illumination mirror 412, on through the illumination polarizer 416 onto the illumination faceted mirror 418. The first illumination source may be a deuterium light source generating a first illumination beam 410 with a wavelength range of about 180 to 400 μm. The second illumination source may be a xenon lamp generating a second illumination beam 414 with a wavelength range of about 200 to 900 nanometers (nm). Alternatively, the first illumination beam 410 may have a wavelength range of 180 to 350 nm and the second illumination beam 414 may have a wavelength range of 300 to 900 nm. Other illumination sources or combination of light sources may be used depending on the desired range of wavelengths generated for the set of illumination beams.

As mentioned above, referring to FIGS. 4, 5B, and 5C, the set of beam separation optics 402 comprises a knife-edge mirror 412, an illumination faceted mirror 418, a detection faceted mirror 490, and a detection knife-edged mirror 498. The illumination faceted mirror 418 of FIG. 4 is further depicted in FIG. 5B in an exemplary embodiment 400A where the first illumination beam 410 is reflected by a first facet 418A as first illumination beam 424 and the second illumination beam 414 is reflected by a second facet 418B as second illumination beam 426. Beams 410 and 414 originate from two spatially-separated point-like sources. After reflecting from facets 418A and 418B, beams 424 and 426 appear to originate from a single point-like virtual source allowing the light from both beams to be eventually focused onto one point on the workpiece. However, beams 424 and 426 are now separated in angle so that they enter separate illumination apertures 420 and 422. Apertures 420 and 422 serve to define the exact shape, NA and angle of incidence of the illumination beams 436 and 434. The angle, β, of the first facet 418A and the second facet 418B can be in the range of 0.3 to 0.8 degrees. Alternatively, the angle of the first facet 418A and the second facet 418B can be in the range of 0.01 to 45.0 degrees. Other facet angles can be used to achieve the spatial separation of the beams desired. A similar detection faceted mirror (490 in FIG. 4) is in the detection path for spatially separating the detection beams (480 and 482) reflected off the detection secondary mirror 474. The detection knife-edged mirror 498 of FIG. 4 is further depicted in FIG. 5C in an exemplary embodiment 400B where the detection beams (494 and 492) are spatially separated and directed to spectroscopic detectors (not shown). The first detection beam 494 is allowed to go through while the second detection beam 492 is reflected by detection knife-edge mirror 498 onto a different spectroscopic detector (not shown). Another knife-edge mirror (412 of FIG. 4) is used to reflect the second illumination beam 414 onto the illumination faceted mirror 418.

Referring to FIG. 4, the illumination secondary mirror 430 is disposed proximate but not connected to the detection secondary mirror 474. The first illumination beam 410 is reflected from the illumination faceted mirror 418, through an illumination aperture 422 as first illumination beam 424 onto the illumination secondary mirror 430, reflected from the illumination secondary mirror 430 onto the illumination primary mirror 432 and reflected onto the structure on the workpiece 440 at a first angle of incidence $\theta_1$. The second illumination beam 414 is reflected from the illumination faceted mirror 418 through an illumination aperture 420 as second illumination beam 426 onto the illumination secondary mirror 430, reflected from the illumination secondary mirror 430 onto the illumination primary mirror 432 and reflected onto the structure (not shown) on the workpiece 440 at a second angle of incidence $\theta_2$. The illumination secondary mirrors 430 and the detection secondary mirror 474 are convex mirrors whereas the primary illumination primary mirror 432 and the detection primary mirror 460 are concave mirrors. In one embodiment, the first angle of incidence, $\theta_1$, can be substantially 30 degrees and the second angle of incidence $\theta_2$, can be substantially 18 degrees. Alternatively, $\theta_1$ can be within a range of 25 to 35 degrees and $\theta_2$ can be within a range of 10 to 22 degrees. Alternatively, $\theta_1$ can be within a range of 40 to 65 degrees and $\theta_2$ can be within a range of 8 to 25 degrees. Other ranges of angles of incidence can also be used.

As mentioned above, use of a separate illumination secondary mirror 430 and a separate detection secondary mirror 474 provide flexibility in achieving desired angles of incidence of the illumination beams onto the structure by adjusting the position and rotation of the secondary mirrors, the primary mirrors, or both relative to the structure. The flexibility of moving the primary mirrors relative to the secondary mirrors to achieve a desire angle of incidence is further enhanced by the absence of an unused portion of a single secondary mirror (321 of FIG. 3). By eliminating mirror section 321 in FIG. 3, the illumination primary and secondary mirrors can be rotated together as one unit about the focus point on the work piece to reduce the angle of incidence. Likewise the same can be done on the collection side to create an objective like the objective lens assembly 404 in FIG. 4. In another embodiment, in order to compensate for the angle of incidence tolerance in manufacturing, a tilt device 442 is capable of matching the tilt of the workpiece 440 to the tilt of the objective lens assembly 404. Furthermore, in another embodiment, the illumination apertures, (420 and 422), are slightly larger than the detection apertures (488 and 486) in part to compensate for the angle of incidence tolerance in manufacturing. The separate secondary mirrors can be utilized to make the angles of incidence as close as possible to the calculated optimum angle of incidence based on numerical aperture of a given light source, such as a deuterium lamp, a xenon lamp, and the kind. Numerical aperture (NA) is determined by taking the sine of the angle of the cone of light generated by the light source. In one embodiment, the NA of the first and second light source is substantially 0.07. Alternatively, the NA of the first and second light sources may be within a range of 0.05 to 0.09. Alternatively, the NA of the first and second light sources may be within a range of 0.07 to 0.12.

Illumination beam 434 is diffracted by the structure on the workpiece 440 as a detection beam 450, reflected by detection primary mirror 460 as detection beam 472 onto the detection convex mirror 474, and reflected as detection beam 480 through the detection aperture 488. Illumination beam 436 is diffracted by the structure on the workpiece 440 as a detection beam 452 and reflected by detection primary mirror 460 as detection beam 470 onto detection secondary convex mirror 474, reflected as detection beam 482 through the detection aperture 486. Both detection beams passing through the detection apertures (486 and 488) onto detection faceted mirror 490, go through detection polarizer 496. As mentioned above, the first detection beam 494 is projected onto a first spectroscopic detector (not shown) and the second detection beam 492 is reflected by detection knife-edged mirror 498 onto a second spectroscopic detector (not shown) where the diffraction signals are measured using the first and second spectroscopic detectors.

Figure 5A:
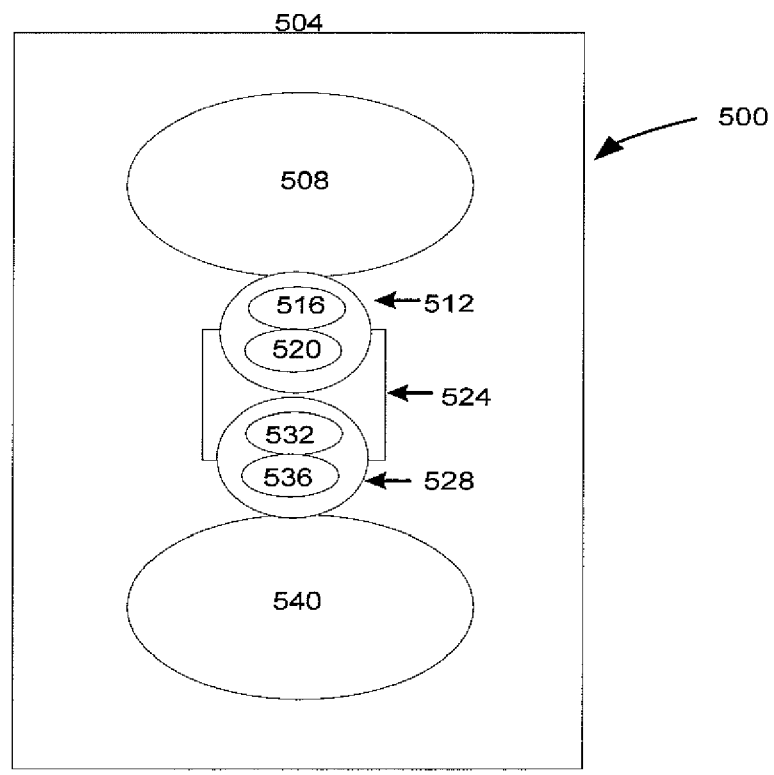
Figure 5B:
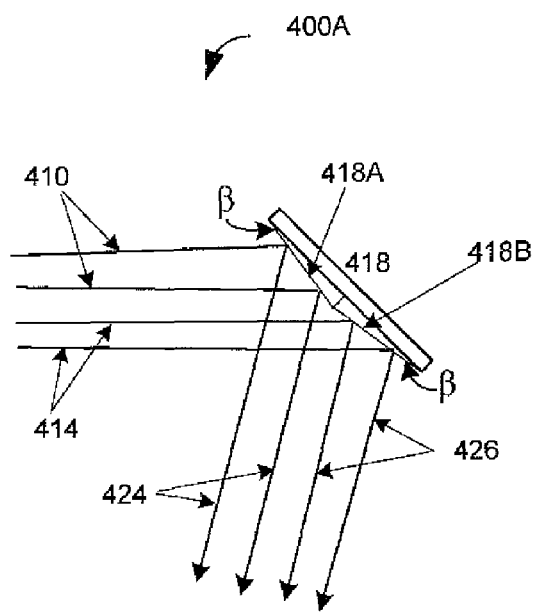
FIG. 5B depicts a facet mirror used to help combine illumination beams from two sources and a similar facet mirror used to help separate two detection beams.
Figure 5C:
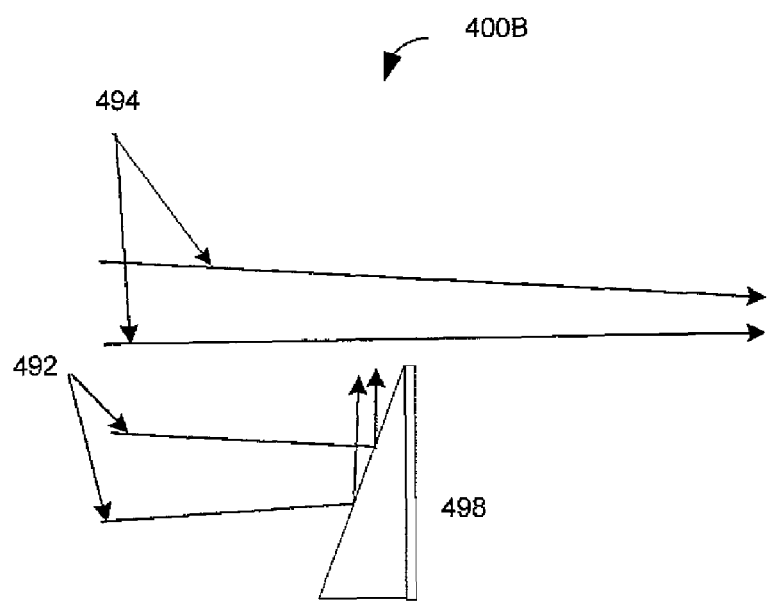
FIG. 5C depicts a knife-edge mirror used to help separate two detection beams, and a similar knife-edge mirror used to help combine two illumination beams.

FIG. 5A depicts a top-view 500 of an architectural diagram of an objective lens assembly using a separate illumination convex secondary mirror for two illumination beams and a separate detection convex secondary mirror such as the one depicted in FIG. 4. With reference to FIG. 5A, the top view 500 of an architectural diagram of an exemplary embodiment utilizing two illumination beams (not shown) comprises a primary illumination mirror 508, a separate illumination secondary mirror 512, and two illumination apertures (532 and 536) of the objective lens assembly 504. The structure (not shown) on the workpiece 524 may or may not be in the center of the objective lens assembly 500 depending on selected footprint and design of the metrology tool. The detection side comprises a primary detection mirror 540, separate detection secondary mirror 528 and two detection apertures (516 and 520) of the objective lens assembly 504.

Figure 6A:
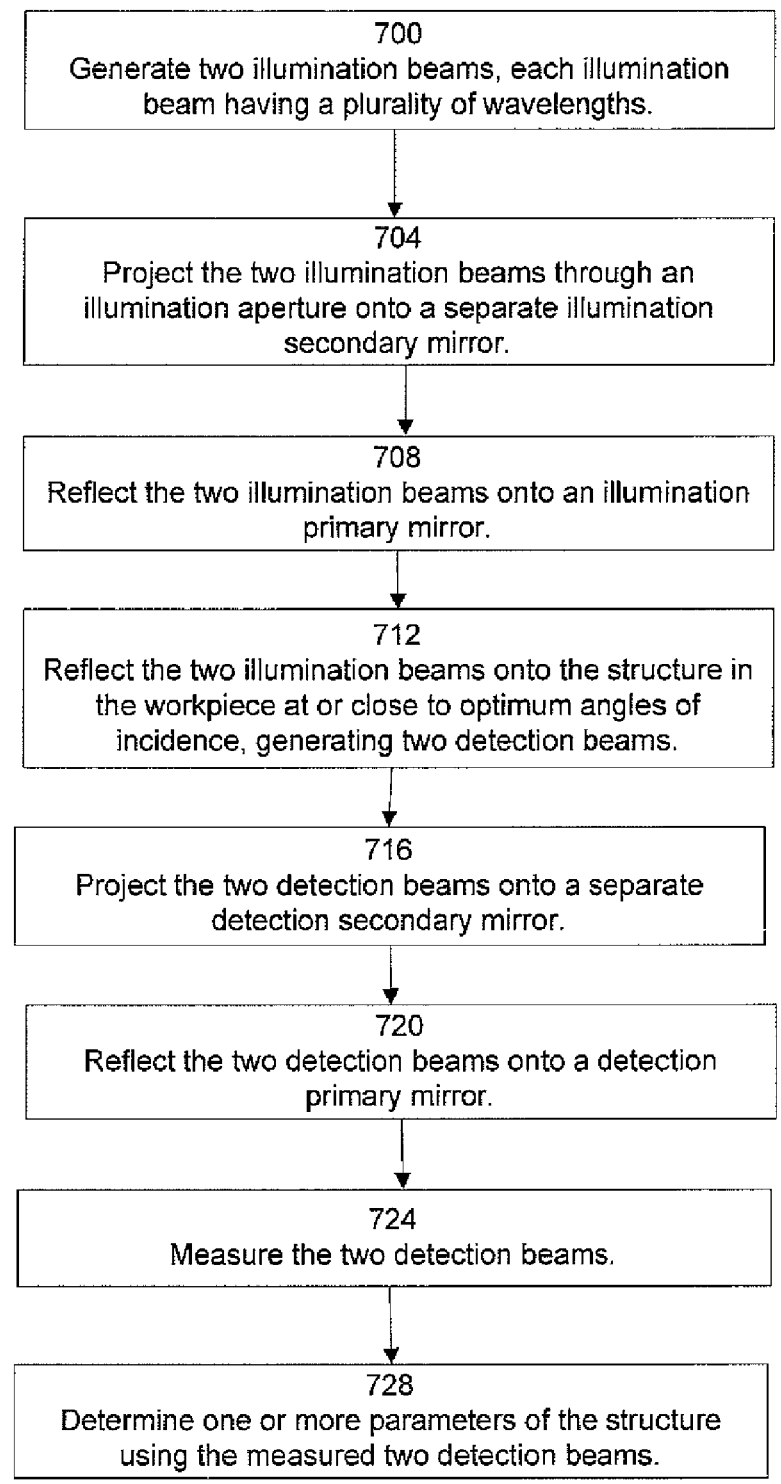
Figure 6B:
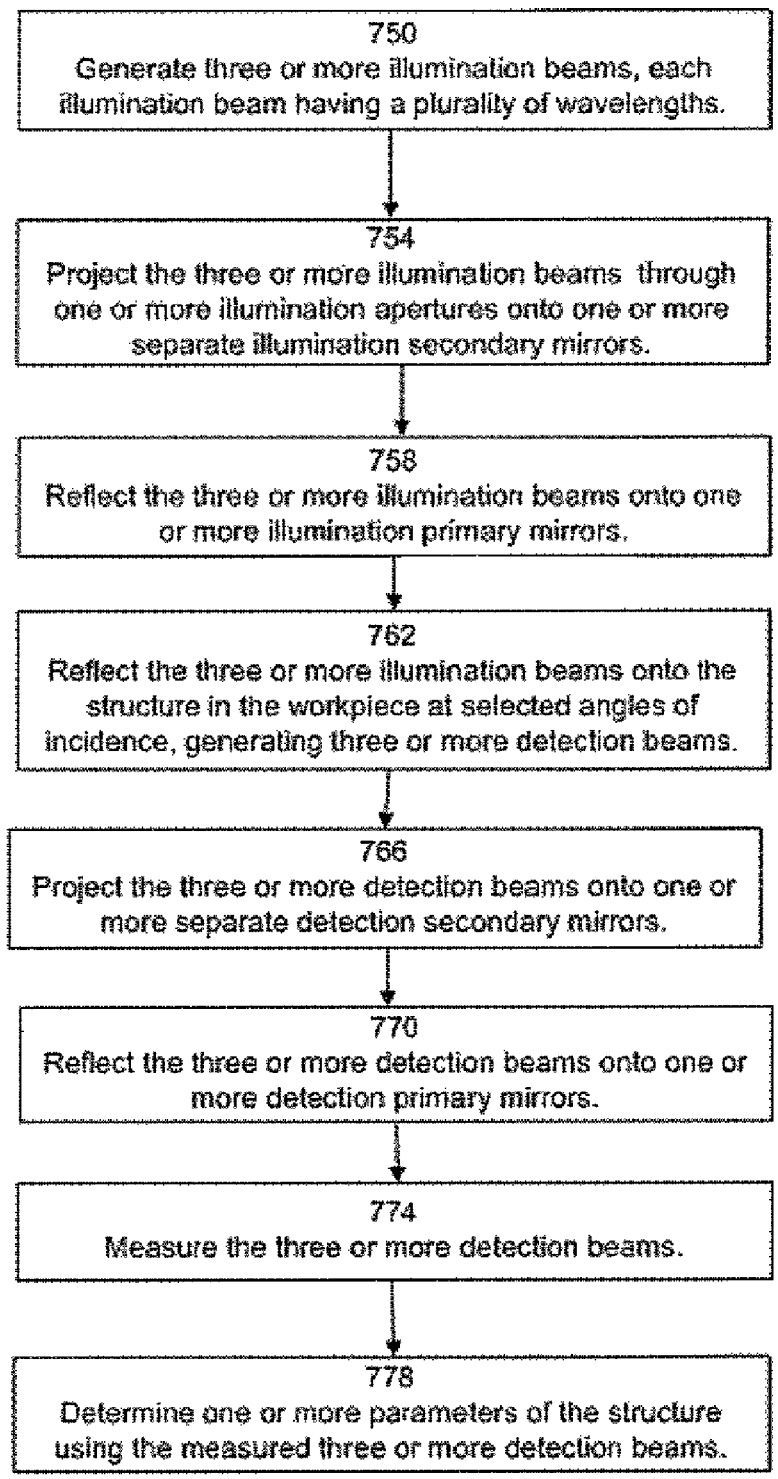
FIG. 6B depicts an exemplary flowchart of a method of determining profile parameters of a structure with an objective lens assembly using separate illumination and detection convex secondary mirrors for three or more illumination beams.

FIG. 6A depicts an exemplary flowchart of a method of determining profile parameters of a structure using an objective lens assembly with two illumination beams whereas FIG. 6B depicts an exemplary flowchart of a method of determining profile parameters of a structure using an objective lens assembly with three or more illumination beams. Referring to FIG. 6A, in step 700, two illumination beams are generated, each beam having a plurality of wavelengths. In one embodiment, a first illumination beam can be generated using a deuterium light source, generating a beam in the range of 180 to 400 nm. A second illumination beam can be generated using a xenon lamp and generates a beam in the range of 200 to 900 nm. Alternatively, the first illumination beam may be in the range of 180 to 380 nm and the second illumination beam may be in the range 180 to 900 nm. Other ranges of wavelengths using other light sources can also be utilized. In step 704, the two illumination beams are projected through a set of beam separation optics, a polarizer, and a corresponding illumination aperture onto an illumination secondary mirror. In one embodiment, the configuration of the illumination secondary mirror is as described for the illumination secondary mirror 430 in FIG. 4. Other configurations of two illumination secondary mirrors can also be used. In step 708, the two illumination beams are reflected onto an illumination primary mirror.

In one embodiment, the illumination primary mirror is a single concave mirror configured such that in combination with the separate illumination secondary mirror, the angles of incidence of the illumination beams onto the structure on the workpiece can be adjusted to be close or equal to a set or calculated optimum angle of incidence based on the numerical aperture of the light sources. In one embodiment, as depicted in FIG. 4, the first angle of incidence, $\theta_1$, can be substantially 30 degrees and the second angle of incidence, $\theta_2$, can be substantially 18 degrees. Alternatively, $\theta_1$ can be within a range of 25 to 35 degrees and $\theta_2$ can be within a range of 10 to 22 degrees. Alternatively, $\theta_1$ can be within a range of 40 to 65 degrees and $\theta_2$ can be within a range of 8 to 25 degrees. Other ranges of angles of incidence can also be used. Still referring to FIG. 6A, the illumination beams reflected from the illumination primary mirror are projected onto the structure on the workpiece at or close to optimum angles of incidence, generating two detection beams, step 712.

In step 716, the two detection beams are reflected onto a separate detection secondary mirror. In step 720, the two detection beams are reflected onto a detection primary mirror, pass through a corresponding detection aperture and other optical components such as a set of beam separation optics and a polarizer. In step 724, the two detection beams are measured using one or more spectroscopic detectors, generating a diffraction signal. In step 728, the diffraction signal is used to determine one or more profile parameters of the structure. For details of using a diffraction signal to determine a structure profile parameter, refer to U.S. Pat. No. 6,943,900, entitled GENERATION OF A LIBRARY OF PERIODIC GRATING DIFFRACTION SIGNAL, issued on Sep. 13, 2005, which is incorporated herein by reference in its entirety and to U.S. patent application Ser. No. 10/608,300, entitled OPTICAL METROLOGY OF STRUCTURES FORMED ON SEMICONDUCTOR WAFERS USING MACHINE LEARNING SYSTEMS, filed on Jun. 27, 2003, which are incorporated herein by reference in their entirety.

FIG. 6B depicts an exemplary flowchart of a method of determining profile parameters of a structure using an objective lens assembly with three or more illumination beams. In step 750, three or more illumination beams are generated, each beam having a plurality of wavelengths. In step 754, the three or more illumination beams are projected through corresponding illumination apertures onto three or more illumination secondary mirrors. In step 758, the three or more illumination beams are reflected onto two or more illumination primary mirrors. In one embodiment, an illumination primary mirror is configured such that in combination with the corresponding illumination secondary mirror, the angle of incidence of each illumination beam onto the structure on the workpiece can be set to be close or equal an optimum angle of incidence based on the numerical aperture of the corresponding light source. The illumination beams reflected from the illumination primary mirrors are projected onto the structure on the workpiece at or close to the optimum angles of incidence, generating three or more detection beams, step 762. In step 766, the three or more detection beams are projected onto detection secondary mirrors. In step 770, the three or more detection beams are reflected onto two or more detection primary mirrors, pass through corresponding detection apertures and other optical components such as beam separation optics and a polarizer. In step 774, the three or more detection beams are measured using two or more spectroscopic detectors, generating a diffraction signal. In step 778, the diffraction signal is used to determine one or more profile parameters of the structure.

Figure 7:
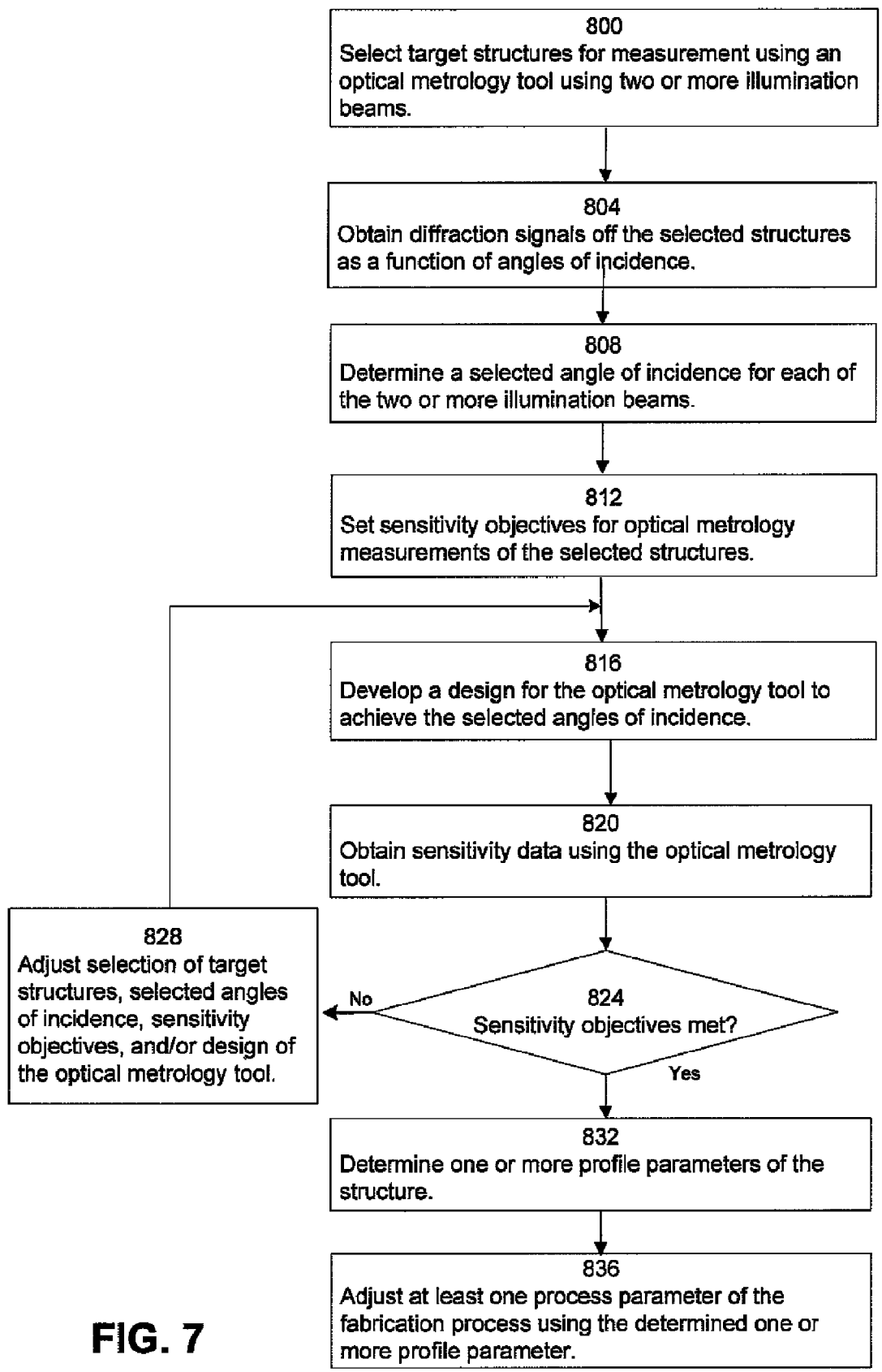
FIG. 7 depicts an exemplary flowchart for optimizing the design of a metrology tool using measurement sensitivity objectives.

FIG. 7 depicts an exemplary flowchart for optimizing the design of a metrology tool using measurement sensitivity objectives. In step 800, target structures are selected for measurement with an optical metrology tool using two or more illumination beams, each illumination beam having a plurality of wavelengths. Target structures may include one or more types of one dimensional repeating structures on a wafer such as gratings, line and space structures, two dimensional repeating structures, and/or complex repeating structures comprising posts, contact holes, vias, islands, and concave or convex three dimensional structures, or combinations of two or more thereof. The optical metrology tool may be a reflectometer, ellipsometer, or hybrid optical metrology tools. In step 804, diffraction signals off the selected structures are obtained as a function of angles of incidence. For example, in a reflectometer, diffraction signals may be obtained to include reflectance intensity measurements as a function of angle of incidence. In ellipsometers, diffraction signals would include intensity and change of polarization as a function of angle of incidence. Diffraction signals may be obtained using actual metrology tools, optical prototypes or numerical simulations. In step 808, an angle of incidence is selected for each of the two or more illumination beams. In one embodiment, for certain selected target structures, the inventors selected to use two illumination beams, namely, one generated using a xenon lamp and another using a deuterium light source. The calculated optimum angle of incidence is substantially 18 degrees for the xenon lamp and substantially 30 degrees for the deuterium light source. Alternatively, the first angle of incidence, $\theta_1$ of FIG. 4, can be within a range of 25 to 35 degrees and the second angle of incidence, $\theta_2$ of FIG. 4, can be within a range of 10 to 22 degrees. Alternatively, $\theta_1$ can be within a range of 40 to 65 degrees and $\theta_2$ can be within a range of 8 to 25 degrees. Other ranges of angles of incidence can also be used.

Figure 8:
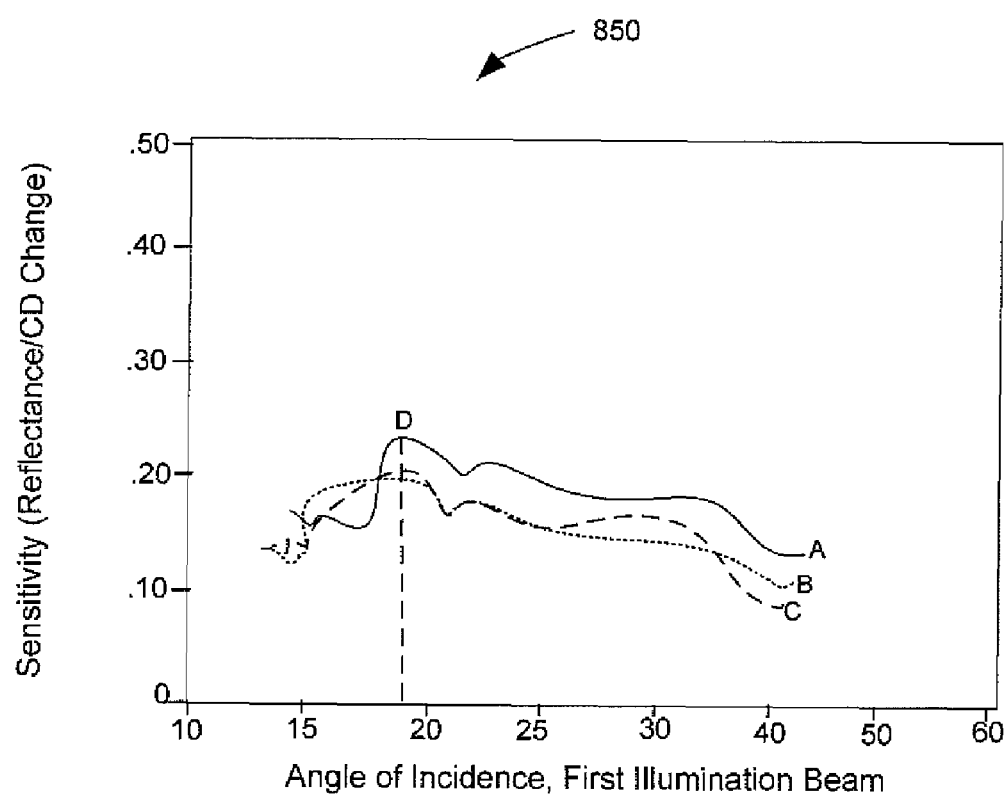
FIG. 8 depicts exemplary graph of optical metrology measurement sensitivity as a function of angle of incidence of the illumination beam.

Selection of the angle of incidence is illustrated in a graph 850 in FIG. 8. The selected angle of incidence can be equal to or close to the calculated optimum angle of incidence. Assume that target structures to be measured with the metrology tool include a line and space grating structure, A, a repeating 2 dimensional structure including contact holes and vias, B, and a combination of isolated and dense structure C. Assume that the metrology tool is a non-normal reflectometer and uses two illumination beams with the first illumination beam generated from a xenon lamp. Also assume that the top critical dimension (CD) of the structures is being measured. The reflectance of the three structures is measured using the reflectometer where critical dimension and the angle of incidence are varied. The changes in normalized reflectance per change in CD width in nanometers are plotted as a function of angle of incidence. Referring to the graph 850, the graphs for the structures A, B, and C depict the highest sensitivity at an angle of incidence of about 18 degrees, at point D. The selected angle of incidence for the first illumination beam in this case would be 18 degrees. Similar graphs or data can also be prepared for the second or subsequent illumination beams and can be used to determine the selected angle of incidence. In another embodiment, the metrology tool is an ellipsometer and change of intensity and polarization are measured and used in the calculations. The selected angle of incidence for an illumination beam may also be verified by simulating the performance of a designed system and comparing to design target specifications.

Referring to FIG. 7, in step 812, measurement sensitivity objectives are set for the selected structures. Based on the selected structures to be measured, certain profile parameters are considered critical dimensions (CDs). Examples of CDs are top width (TCD), mid width (MCD) and bottom width (BCD). Other profile parameters are often included, such as grating heights, sidewall angle, and the like. Using the example above, assume that the TCD is critical for the selected structures, measurement sensitivity can be simulated with an algorithm such as RCWA as the reflectance change per 1 nm change of the TCD. The simulated sensitivity can be used to verify if the design can meet the desired measurement requirements, such as accuracy and precision. Sensitivity for one or more different CDs may be calculated concurrently. In step 816, a design is developed for the optical metrology tool to achieve the selected angles of incidence. In one embodiment, as depicted and described in connection with FIG. 4, a separate illumination secondary mirror is used in the illumination path and a separate detection secondary mirror is used in the detection path for an optical metrology tool with two illumination beams. Other configurations using three or more beams can also be used.

In step 820, sensitivity data using the optical metrology tool is obtained. Sensitivity data may be obtained using a variety of techniques including using an assembled or manufactured version of the optical metrology tool, using an optical breadboard prototype that includes the essential components developed in the design in step 816, or using simulation of the diffraction signal using metrology modeling techniques. Use of an optical breadboard prototype is discussed in detail in application Ser. No. 12/050,053 entitled METHOD OF DESIGNING AN OPTICAL METROLOGY SYSTEM OPTIMIZED FOR OPERATING TIME BUDGET, filed on Mar. 17, 2008, which is incorporated herein by reference in its entirety. In step 820, the sensitivity data obtained using the optical metrology tool is compared to the set sensitivity objectives. If the set sensitivity objectives are met, then one or more profile parameters of the structure is determined using a diffraction signal measured off the structure using the optical metrology tool, step 832. The determined one or more profile parameters is used to adjust at least one process parameter of the current fabrication process of the workpiece, or a subsequent process or a prior process, step 836.

Referring to step 824 of FIG. 7, if the set sensitivity objectives are not met, the selection of target structures, the selected angles of incidence, the sensitivity objectives, and/or the design of the optical metrology tool are adjusted, and developing of the optical metrology design, obtaining sensitivity data using the optical metrology tool, and comparing sensitivity data obtained using the optical metrology tool compared to the set sensitivity objectives are iterated until the set sensitivity objectives are met. Adjusting the selection of target structures may include identifying a structure that cannot be accurately measured by the optical metrology tool and excluding this type of structure in the latter parts of the method. Adjusting the selected angles of incidence may include changing the selected angle of incidence based on new or more extensive diffraction signal data. The sensitivity objectives may be raised or lowered based on the structure application or fabrication requirements. The design of the optical metrology tool may be adjusted by selecting different light sources, changing the number of illumination beams, changing the set of wavelengths included in an illumination beam, altering the design of the objective lens assembly, and/or using different optical components or a combination of two or more of the foregoing. As described in relation to FIGS. 4 and 5A, the design of the objective lens assembly can be changed to use separate illumination and detection secondary mirrors to provide the flexibility of achieving or getting close to an optimum angle of incidence when the numerical aperture of the beam is fixed.

Figure 9:
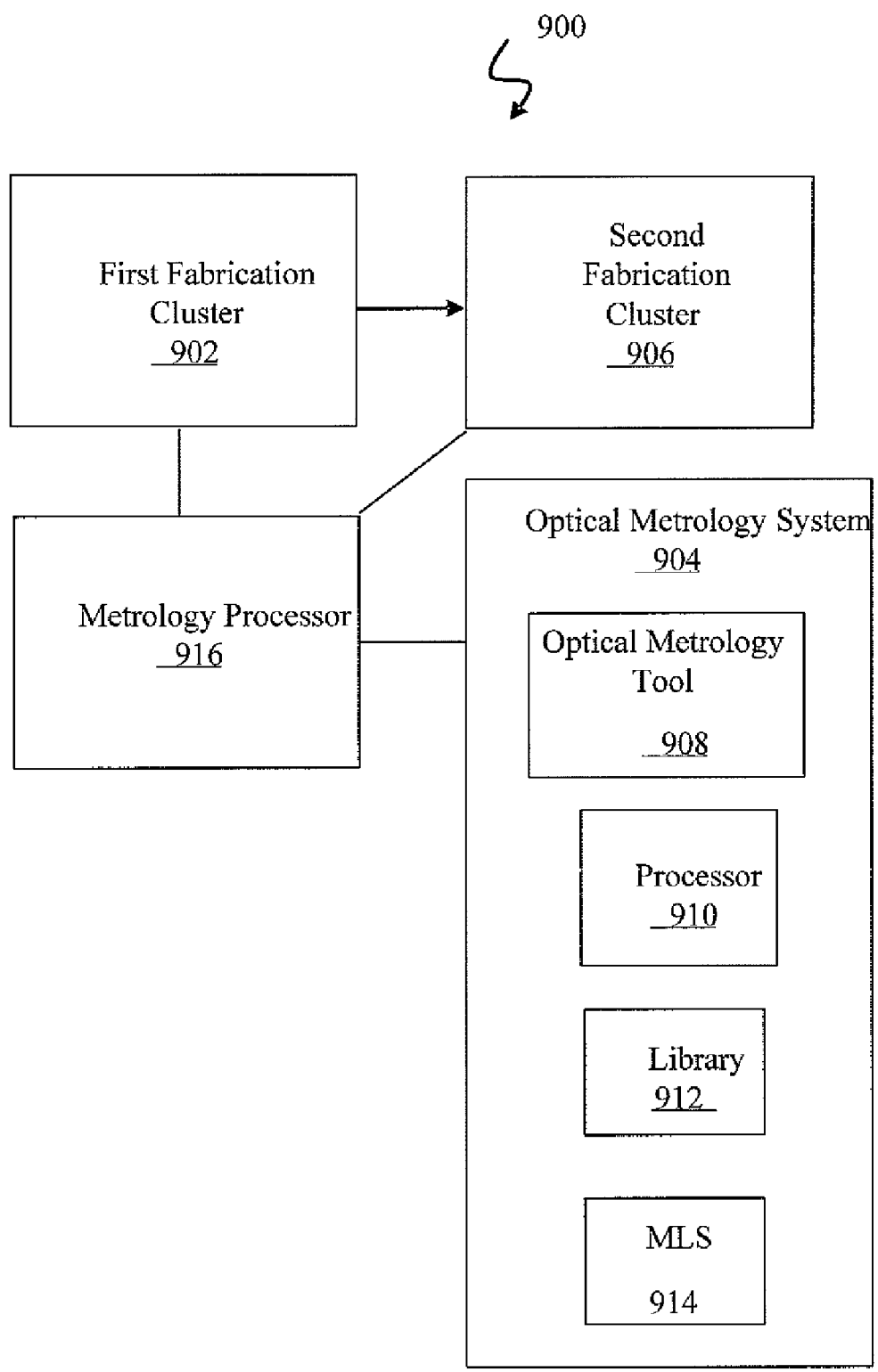
FIG. 9 depicts an exemplary prior art block diagram of a system for determining and utilizing profile parameters for automated process and equipment control.

FIG. 9 is an exemplary prior art block diagram of a system for determining and utilizing profile parameters for automated process and equipment control. System 900 includes a first fabrication cluster 902 and optical metrology system 904. System 900 also includes a second fabrication cluster 906. Although the second fabrication cluster 906 is depicted in FIG. 9 as being subsequent to first fabrication cluster 902, it should be recognized that second fabrication cluster 906 can be located prior to first fabrication cluster 902 in system 900 (e.g. and in the manufacturing process flow).

A photolithographic process, such as exposing and/or developing a photoresist layer applied to a wafer, can be performed using first fabrication cluster 902. Optical metrology system 904 is similar to optical metrology system 40 of FIG. 1. In one exemplary embodiment, optical metrology system 904 includes an optical metrology tool 908 and processor 910. Optical metrology tool 908 is configured to measure a diffraction signal off of the structure. The optical metrology tool 908 can include an objective lens assembly as depicted in FIG. 4. Processor 910 is configured to compare the measured diffraction signal measured by the optical metrology tool designed to meet plurality of design goals to a simulated diffraction signal. As mentioned above, the simulated diffraction is determined using a set of profile parameters of the structure and numerical analysis based on the Maxwell equations of electromagnetic diffraction. In one exemplary embodiment, optical metrology system 904 can also include a library 912 with a plurality of simulated diffraction signals and a plurality of values of one or more profile parameters associated with the plurality of simulated diffraction signals. As described above, the library can be generated in advance; metrology processor 910 can compare a measured diffraction signal off a structure to the plurality of simulated diffraction signals in the library. When a matching simulated diffraction signal is found, the one or more values of the profile parameters associated with the matching simulated diffraction signal in the library is assumed to be the one or more values of the profile parameters used in the wafer application to fabricate the structure.

System 900 also includes a metrology processor 916. In one exemplary embodiment, processor 910 can transmit the one or more values of the one or more profile parameters to metrology processor 916. Metrology processor 916 can then adjust one or more process parameters or equipment settings of the first fabrication cluster 902 based on the one or more values of the one or more profile parameters determined using optical metrology system 904. Metrology processor 916 can also adjust one or more process parameters or equipment settings of the second fabrication cluster 906 based on the one or more values of the one or more profile parameters determined using optical metrology system 904. As noted above, second fabrication cluster 906 can process the wafer before or after first fabrication cluster 902. In another exemplary embodiment, processor 910 is configured to train machine learning system 914 using the set of measured diffraction signals as inputs to machine learning system 914 and profile parameters as the expected outputs of machine learning system 914

Figure 10:
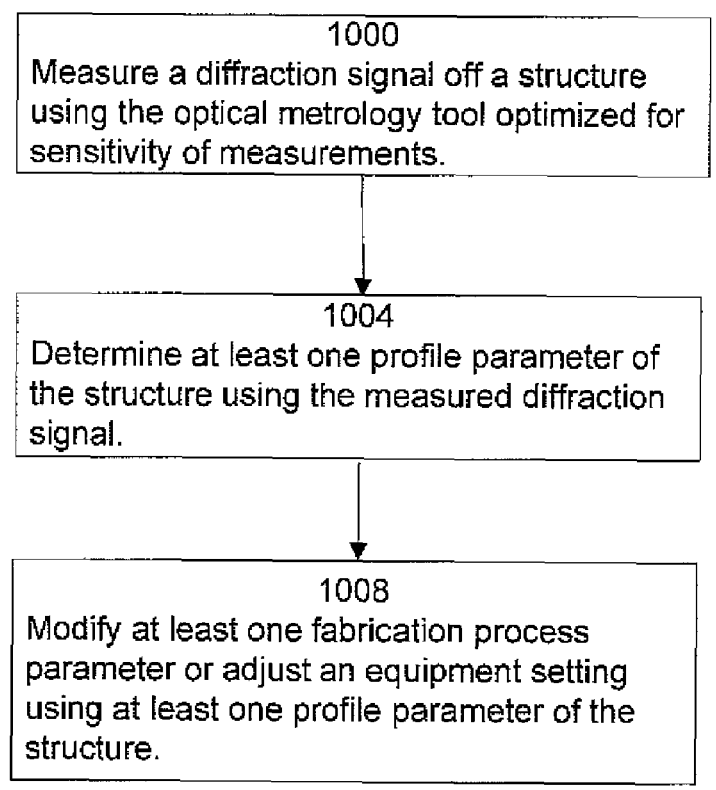
FIG. 10 depicts an exemplary prior art flowchart for optical metrology measurements of a structure on the workpiece, extracting structure profile parameters and controlling a fabrication process.

FIG. 10 depicts an exemplary prior art flowchart for optical metrology measurements of a structure on the workpiece, extracting structure profile parameters and controlling a fabrication process. In step 1000, one or more diffraction signals off a target structure on the workpiece are measured with an optical metrology system, where the metrology system includes a metrology tool with an objective lens assembly as depicted in FIG. 4. In step 1004, at least one profile parameter of the structure is determined using the measured diffraction signals. If the workpiece is a semiconductor wafer, the one profile parameter may be a top critical dimension (CD), a bottom CD, or a sidewall angle. In step 1008, at least one fabrication process parameter or equipment setting is modified using the determined at least one profile parameter of the structure. For example, if the workpiece is a wafer, the fabrication process parameter may include a temperature, exposure dose or focus, etchant concentration or gas flow rate. As mentioned above, the optical metrology system may be part of a standalone metrology module or integrated in a fabrication cluster.

Although exemplary embodiments have been described, various modifications can be made without departing from the spirit and/or scope of the present invention. For example, although an optical metrology tool with two illumination beams was primarily used to describe the embodiments of the invention; other configurations with three or more illumination beams may also be used as mentioned above. For automated process control, the fabrication clusters may be a track, etch, deposition, chemical-mechanical polishing, thermal, or cleaning fabrication cluster. Furthermore, the optical metrology tool designed using the methods and apparatus of the invention are substantially the same regardless of whether the optical metrology tool is integrated in a fabrication cluster or used in a standalone metrology setup. Therefore, the present invention should not be construed as being limited to the specific forms shown in the drawings and described above.

What is claimed:

1. A method of performing optical metrology with multiple beams directed to a structure in a workpiece, the method comprising:
    generating a first illumination beam having a first plurality of wavelengths using a first light source;
    generating a second illumination beam having a second plurality of wavelengths using a second light source;
    projecting the first and second illumination beams onto an illumination secondary mirror;
    reflecting the first and second illumination beams onto an illumination primary mirror, the reflected first and second illumination beams projected onto a structure on the workpiece at a first angle of incidence and a second angle of incidence respectively, the reflected first and second illumination beams generating a first and second detection beams respectively;
    projecting the first and second detection beams onto a detection primary mirror, generating an output first and second detection beams; and
    reflecting the output first and second detection beams onto a detection secondary mirror;
    wherein an optimum first angle of incidence is derived based on the first light source and a calculated numerical aperture of the first illumination beam and an optimum second angle of incidence is derived based on the second light source and a calculated numerical aperture of the second illumination beam;
    wherein the illumination primary mirror and illumination secondary mirror are positioned so as to make the first angle of incidence substantially equal or close to the optimum first angle of incidence and the second angle of incidence substantially equal or close to the optimum second angle of incidence;
    wherein the detection secondary mirror is positioned relative to the detection primary mirror so as to reflect the first detection beam through a first detection aperture and the second detection beam through a second detection aperture; and wherein the illumination secondary mirror is a single piece mirror and the detection secondary mirror is a single piece mirror, the illumination secondary mirror located proximate to the detection secondary mirror.

2. The method of claim 1 wherein the numerical aperture of the first illumination beam and second illumination beam are substantially 0.07 or within the range of 0.05 to 0.09.

3. The method of claim 1 wherein the first light source is a deuterium light source and the second light source is a xenon lamp or wherein the first plurality of wavelengths ranges from 180 to 400 nanometers and the second plurality of wavelengths ranges from 200 to 900 nanometers.

4. The method of claim 1 wherein the illumination secondary mirror is a single piece convex mirror and the detection secondary mirror is a single piece convex mirror.

5. The method of claim 1 wherein the first angle of incidence is substantially 30 degrees or within a range of 25 to 35 degrees.

6. The method of claim 1 wherein the second angle of incidence is substantially 18 degrees or within a range of 10 to 22 degrees.

7. The method of claim 1 wherein the first and second illumination beams are deviated to appear to originate from a single virtual source and reflected through corresponding illumination apertures using an illumination knife-edged mirror and an illumination faceted mirror.

8. The method of claim 1 wherein the first and second detection beams are spatially separated and reflected onto corresponding detectors using a detection knife-edged mirror and a detection faceted mirror.

9. The method of claim 1 wherein the illumination primary mirror, the illumination secondary mirror, the detection aperture, the detection primary mirror, and the detection secondary mirror are components of an objective lens assembly.

10. The method of claim 9 wherein the workpiece is a wafer, a substrate, or a photomask.

11. The method of claim 9 further comprising tilting the workpiece to match the horizontal orientation of the objective lens assembly.

12. The method of claim 9 wherein the objective lens assembly is a component of an optical metrology tool.

13. The method of claim 12 wherein the optical metrology tool is used to measure diffraction signals off the structure, the structure having profile parameters.

14. The method of claim 13 wherein the diffraction signals are used to determine at least one profile parameter of the structure.

15. The method of claim 14 wherein determination of at least one profile parameter of the structure utilizes a library or a trained machine learning system.

16. A method of performing optical metrology using two or more beams directed to a structure on a workpiece, the structure having profile parameters, the method comprising:

generating two or more illumination beams, each illumination beam generated by a light source and having a plurality of wavelengths;

projecting the two or more illumination beams onto one or more illumination secondary mirrors;

reflecting the two or more illumination beams onto one or more illumination primary mirrors, the reflected two or more illumination beams projected onto the structure, each of the reflected two or more illumination beams at an angle of incidence, the reflected two or more illumination beams generating two or more detection beams;

projecting the two or more detection beams onto one or more detection primary mirrors generating as output two or more detection beams; and reflecting the output two or more detection beams onto one or more detection secondary mirrors;

measuring the output two or more detection beams using two or more spectroscopic detectors, the measurement generating a diffraction signal;

wherein an optimum angle of incidence is derived for each of the two or more illumination beams based on the light source and a corresponding calculated numerical aperture, generating two or more optimum angles of incidence; and wherein the each of the one or more illumination primary mirrors together with the corresponding one of the one or more illumination secondary mirrors are positioned to make the corresponding one of the two or more angles of incidence substantially equal or close to the corresponding optimum angle of incidence of the two or more optimum angles of incidence.

17. The method of claim 16 wherein the two or more illumination beams comprise three illumination beams.

18. The method of claim 16 wherein a first angle of incidence is substantially 30 degrees or within a range of 25 to 35 degrees and a second angle of incidence is substantially 18 degrees or within a range of 10 to 22 degrees.

19. The method of claim 16 wherein the numerical aperture of the first and second illumination beams of the two or more illumination beams is substantially 0.07 or within the range of 0.05 to 0.09.

20. The method of claim 16 further comprising:

determining one or more profile parameters of the structure from the diffraction signal.

* * * * *